(12) United States Patent
Chung et al.

(10) Patent No.: US 7,033,788 B2
(45) Date of Patent: Apr. 25, 2006

(54) **PROTEIN DERIVED FROM *AGKISTRODON SAXATILIS EMELIANOV* AND PROCESS PREPARING THE SAME**

(75) Inventors: Kwang-Hoe Chung, 101-1305 Mooakcheonggu Apartment Hongie-dong, Seodaemoon-gu, Seoul (KR); Doo-sik Kim, 84-3 Yeohee-dong, Seodaemoon-gu, Seoul (KR); Sung-Yu Hong, Kyunggi-Do (KR); You-Seok Koh, Seoul (KR); Young-Doug Sohn, Kyunggi-Do (KR); Weon-Kyoo You, Seoul (KR); Yang-Soo Jang, Kyunggi-Do (KR); Chin-Kyu Huh, Seoul (KR)

(73) Assignees: Kwang-Hoe Chung, Seoul (KR); Doo-sik Kim, Seoul (KR)

( * ) Notice: Subject to any disclaimer, the term of this patent is extended or adjusted under 35 U.S.C. 154(b) by 675 days.

(21) Appl. No.: 10/089,473

(22) PCT Filed: Mar. 26, 2002

(86) PCT No.: PCT/KR00/00809

§ 371 (c)(1),
(2), (4) Date: Mar. 26, 2002

(87) PCT Pub. No.: WO02/14488

PCT Pub. Date: Feb. 21, 2002

(65) Prior Publication Data

US 2005/0032189 A1    Feb. 10, 2005

(51) Int. Cl.
*C12N 15/12* (2006.01)
*C12N 15/63* (2006.01)
*C12N 1/19* (2006.01)
*C12N 1/00* (2006.01)
*A61K 38/17* (2006.01)

(52) U.S. Cl. ............. 435/69.1; 435/320.1; 435/254.23; 435/254.11; 435/252.3; 514/12; 530/300; 530/324; 536/23.5

(58) Field of Classification Search ............... 536/23.5; 530/324, 300; 514/12; 435/69.1, 320.1, 435/254.23, 254.11, 252.3
See application file for complete search history.

(56) References Cited

U.S. PATENT DOCUMENTS 6,013,625 A      1/2000   Pierschbacher et al. ........ 514/9
6,753,315 B1 *   6/2004   Hawrot ....................... 514/12

FOREIGN PATENT DOCUMENTS

KR    1997-006318    1/2000

OTHER PUBLICATIONS

Smith J B et al. Identification Of 50 Kda Snake Venom Proteins Which Specifically Inhibit Platelet Adhesion To Collagen (199 Febs Letters 283 (2-3):p307-310.*
Callard et al. The Cytokine FactsBook. 1994 New York: Academic Press. p. 31.*
Hong et al. Snake venom disintegrin, saxatilin,inhibits platelet aggregation, human umbilical vein endothelial cell proliferation, and smooth muscle cell migration. Jan. 1, 2002. Thrombosis research 105(1): p79-86.*
Chen et al. Classification of Agkistrodon species in China. 1984. Toxicon 22(1) p53-61.*
Kogan et al. 1991 Comparative Study of Protein C Activators from the Agkistrodon snake venoms. 1991 Thrombosis Research 62 (6): pp 775-780.*
Kang, In-Cheol et al., A Novel Disintegrin Salmosin Inhibits Tumor Angiogenesis, *Cancer Res.*, 59:3754-3760 (1999).
Park, Dongsu et al., Cloning and Characterization of Novel Disintergrins from *Agkistrodon halys* Venom, *Mol. Cells*, 8(5):578-584 (1998).
Kang, in-Cheol et al., Suppressive Mechanism of Salmosin, a Novel Disintegrin in B16 Melanoma Cell Metastasis, *Biochemical and Biophysical Research Communications.*, 275(1):169-173 (2000).
Hong, Sung-Yu et al., Snake Venom Disintegrin, Saxatilin, Inhibits Platelet Aggregation, Human Umbilical Vein Endothelial Cell Proliferation, and Smooth Muscle Cell Migration, *Thrombosis Res.*, 105:79-86 (2002).
Koh, You-Seok et al., Biochemical Characterization of a Thrombin-like Enzyme and a Fibrinolytic Serine Protease from Snake (*Agkistrodon saxatilis*) Venom, *Toxicon*, 39:555-560 (2001).

(Continued)

*Primary Examiner*—Gabriele Bugaisky
(74) *Attorney, Agent, or Firm*—Darby & Darby

(57) ABSTRACT

The present invention relates to Saxatilin, a protein derived from the venom of a Korean snake, *Agkistrodon saxatilis emelianov*, a process for preparing Saxatilin, and pharmaceutical application of the same as anti-platelet aggregation agent and anti-tumor agent. The present inventors purified Saxatilin from the venom of *Agkistrodon saxatilis emelianov*, cloned its cDNA, and prepared recombinant Saxatilin by culturing a microorganism transformed with an expression vector containing the cDNA. Saxatilin effectively suppresses the platelet aggregation and angiogenesis of tumor cells, which makes possible its practical application as an active ingredient of anti-platelet agent and anti-tumor agent.

13 Claims, 8 Drawing Sheets

OTHER PUBLICATIONS

Matsui, Taei et al., Purification and Amino Acid Sequence of Halystase from Snake Venom of *Agkistrodon halys blomhoffii,* a Serine Protease that Cleaves Specifically Fibrinogen and Kininogen, *Eur. J. Biochem.,* 252:569-575 (1998).

Kang, In-Cheol et al., Purification and Molecular Cloning of a Platelet Aggregation Inhibitor from the Snake (*Agkistrodon Halys Brevicaudus*) Venom, *Thrombosis Res.,* 91:65-73 (1998).

\* cited by examiner

PROTEIN DERIVED FROM *AGKISTRODON SAXATILIS EMELIANOV* AND PROCESS PREPARING THE SAME

BACKGROUND OF THE INVENTION

1. Field of the Invention

The present invention relates to Saxatilin, a protein derived from a Korean snake, *Agkistrodon saxatilis emelianov*, a process for preparing Saxatilin, and pharmaceutical application of the same, more specifically, to Saxatilin, a protein derived from the venom of a Korean snake, *Agkistrodon saxatilis emelianov*, a process for preparing Saxatilin, and pharmaceutical application of the same as anti-platelet aggregation agent and anti-tumor agent.

2. Description of the Prior Art

Tumor invasion and metastasis are defined as the proliferating stages of the tumor cells at whole body from the primary tumor, which finally persuade the patient into death. Cancer cells detached from the primary malignant neoplasm (mostly endothelium) penetrate the basement membrane which separates the cancer cells from the other tissue. As some penetrated cells can invade not only endothelium but also basement membrane which surrounds the blood vessels, they can migrate freely via blood vessels and finally set down on capillary vessels. If cancer cells penetrate capillary vessels again, they can form a secondary tumor. The probability of secondary tumor formation from the primary tumor followed by dissemination and invasion is under one in ten thousand (see: Erkki R., Scientific American, 257: 72–77 (1996)).

The interaction of cell and extracellular matrix (ECM) is required for the tumor invasion and metastasis. During metastasis, tumor cells induce endothelial cell death, leading to exposure of basement membrane, which facilitates adhesion of tumor cells with ECM protein in surrounding stroma (see: Hynes, R. O., Cell, 48:549(1987)). These substrate proteins promote cell adhesion by binding with cell surface receptor including integrin family.

In terms of structure, each integrin is a heterodimer formed by $\alpha$ subunit and $\beta$ subunit via non-covalent binding. It has been reported that $\beta 1$ subfamily plays a role in cell-cell interaction directly as well as in cell-ECM substrate adhesion as a major contact mediator (see: Larjava, H. et al., J. Cell. Biol., 110:803–815 (1990)). $\beta 2$ subfamily distributed in leukocyte includes cell surface receptors which mediate cell-cell interaction. $\beta 3$ subfamily including vitronectin receptor and thrombocyte glycoprotein IIb/IIIa complex may be able to function in the development of tumor invasiveness and in the progress of tumor into the malignant tumor (see: Albelda, S. M. et al., Cancer Res., 50:6757–6764 (1990)).

The integrin receptor complex that transversely spans the cell membrane plays a role in connecting cytoskeletal network with extracellular matrix. The core sequences, common to cell-adhesion molecules like fibrinogen, vitronectin and laminin are known to be responsible for cell adhesion, spread and integration. By the way, it is also suggested that cancer promotion and metastasis can be closely related to the role of integrin (see: Giancotti, F. G. and Rouslahti, E., Cell, 60:849–859 (1990); Hynes, R. O., Cell, 69:11–25 (1992); Nip, J. et al., J. Clin. Invest., 30 96:2096–2103 (1995)). Over-expression of fibronectin receptor $\alpha 5\beta 1$ is known to diminish a mutated phenotype in CHO (Chinese hamster ovary) and decrease the expression level of integrin $\alpha 5\beta 1$ in the rodents cells which are mutated into ras (see: Plantefaben, L. C. and Hynes, R. O., 35 Cell, 56:281–290 (1989)). Super-fibronectin, a fibronectin polymer, has been reported to prevent cancer promotion and metastasis (see: Pasqualini, R. et al., Nature Medicine, 2:1197–1203 (1996)).

Integrin $\alpha V\beta 3$ can be useful as a marker of most malignant tumor cells, which shows the function of integrin in the development of malignant human melanoma (see: Albelda, S. M. et al., Cancer Res., 50:6757–6764(1990)). The expression and adhesive phenotype of integrin $\alpha V$ gene have a direct correlation with in vivo proliferation of human melanoma (see: Felding-Habermann, J. Clin. Invest., 89:2018–2022 (1992)).

Meanwhile, angiogenesis is the process of new blood vessels formation by sprouting of new vessels from existing blood vessels (see: Folkman, J. and D'Amore, P. A., Cell, 87:1153–1155 (1996)). Angiogenesis occurs during development, wound healing and inflammation, and is the essential process in the tumor growth. Cell-adhesion molecules regulate angiogenesis in smooth muscle cells and capillary endothelial cells (see: Nguyen, M. et al., Nature, 365:267 (1993)).

The turnover of tumor angiogenesis is determined by the balance change between stimulating and inhibiting regulators. In relation to this, two cytokine-dependent pathways of angiogenesis have existed and are distinguished by the distinct vascular cell integrins, $\alpha V\beta 3$ and $\alpha V\beta 5$. These two integrins are expressed in newly formed blood vessels and play an important role in angiogenesis stimulated by bFGF (basic fibroblast growth factor), TNF-$\alpha$ (tumor necrosis factor-$\alpha$), VEGF (vascular endothelial growth factor) and fragments of human tumors (see: Friedlander, M. et al., Science, 270:1500–1502 (1995)). The activation of $\alpha V\beta 3$ integrin stimulates a survival signal inducing the vessel proliferation and differentiation, which demonstrates that the signal transmission by cytokine and integrin receptor is related to angiogenesis (see: Brooks, P. C. et al., Cell, 79:1157–1164 (1994)).

Disintegrins, which are known to be potent antagonists of integrin, are small proteins derived from snake venom (see: Niewiarowski, S. et al., Semin. Hematol., 31:289–300(1994)). Most of disintegrins contain Arg-Gly-Asp (GRD) or Lys-Gly-Asp (KGD) motifs recognized by thrombocyte fibrinogen receptor, $\alpha 2b\beta 3$. It is reported that disintegrins containing RGD sequences inhibit adhesion of integrin-mediated metastatic cells with ECM and finally block metastasis (see: Trikha, M. et al., Cancer Res., 54 (8):4993–4998(1994)). Integrin $\alpha V\beta 3$ has been identified as a marker of angiogenic vessels in chicken embryo and human cells (see: Brooks, P. C. et al., Science, 264:569–571 10(1994)). Monoclonal antibody of integrin $\alpha V\beta 3$ disrupts angiogenesis by inducing apoptosis of the newly formed vascular endothelial cells. Synthesized peptides containing RGD sequence, which is known to prevent integrin $\alpha V\beta 3$ from binding with ligands, inhibit tumor-induced angiogenesis (see: Brooks, P. C. et al., Cell, 79:1157–1164(1994)) of CAM (chick chorioallantoic membrane). Furthermore, Angiogenin, which is known to help adhesion and proliferation of endothelial cell as a subsidiary factor, is also inhibited by synthesized RGD peptides. Recently, the snake venom-derived disintegrin, Triflavin was reported to inhibit TNF-$\alpha$ stimulated angiogenesis. These results provide the possibility that disintegrins, synthesized RGD peptides and anti-$\alpha V\beta 3$ monoclonal antibodies, may be developed as anti-cancer drugs.

On the other hand, the snake venom is known to contain various kinds of proteins that affect thrombosis and hemostasis. Since thrombus formation resulted from the abnormal platelet coagulation raises lethal thrombosis, platelet aggregation antagonist or agonist was isolated from the snake venom and identified. As for aggregation mechanism, platelet aggregation is mediated by fibrinogen binding with a glycoprotein in the platelet of GP IIb/IIIa receptor, where the amino acid sequence of Arg-Gly-Asp (RGD) of fibrinogen binding site has been reported to be crucial for fibrinogen binding with GP IIb/IIIa receptor (see: Rouslagti E. and Pierschbacher M. D., Science, 238:491–497 (1987)). Therefore, proteins containing the said sequence competitively inhibit fibrinogen binding with GP IIb/IIIa receptor which leads to the suppression of platelet aggregation. At first, inhibitors of GP IIb/IIIa receptor isolated from the snake venom were small proteins of 5 kD to 9 kD (see: Huang, T. F. et al., J. Biol. Chem., 262:16157–16163 (1987)). Afterwards, various kinds of platelet aggregation inhibitors, which included large molecular weight antagonists, were isolated from the snake venom. These inhibitors are rich in cysteins, and common in binding with GP IIb/IIIa receptor by the interaction with the Arg-Gly-Asp (RGD) amino acid sequence. In addition, the structures of Kistrin (see: Alder, M. et al., Science, 253:445–448 (1991); Alder, M. et al., Biochemistry, 32: 282–289 (1993)), Flavoridine (see: Klaus, W. et al., J. Mol. Biol., 232:897–906 (1993); Senn, H. and Klaus, W., J. Mol. Biol., 232:907–925 (1993)), Albolabrin (see: Jaseja, M. et al., Eur. J. Biochem., 218: 853–860 (1993)) and Echistatin (see: Chen, Y. et al., Biochemistry, 30:11625–11636 (1991); Cooke, R. M. et al., Eur. J. Biochem., 202:323–328 (1991); Cooke, R. M. et al., Protein Eng., 5:473–477 (1992); Saudek, V. et al., Biochemistry, 30:7369–7372 (1991); Dalvit, C. et al., Eur. J. Biochem., 202:315–321 (1991)) have been identified by nuclear magnetic resonance (NMR) spectroscopy. And, the inhibition of fibrinogen binding with GP IIb/IIIa receptor by these antagonists was ascertained by using animal model (see: Collen, B. S., J. Clin. Invest., 76:101–108 (1985); Gold, H. K. et al., Circulation, 77:670–677 (1988); Yasuda, T. et al., J. Clin. Invest., 81:1284–1291 (1988); Coller, B. S. et al., Blood, 68:783–786 (1986); Hanson, S. R. et al., J. Clin. Invest., 81:149–158 (1988)).

In relation to this, extensive studies have been made on the venom of *Agkistrodon halys brevicaudus* or *Caliginosus*. Salmosin derived from the venom of *Agkistrodon halys brevicaudus*, a protein of about 7.5 kD, has been proposed as a potent platelet aggregation inhibitor (see: Korean Patent No. 142606). However, little is known about the venom of *Agkistrodon saxatilis emelianov* because of the rareness of *Agkistrodon saxatilis emelianov* compared with other snakes. This invention was made on the assumption that the potent toxicity and high lethality of *Agkistrodon saxatilis emelianov* venom may be closely related with the bleeding.

SUMMARY OF THE INVENTION

The present inventors examined the existence of a protein which plays a role as platelet aggregation inhibitor from the venom of a Korean snake, *Agkistrodon saxatilis emelianov*, and discovered a novel protein, Saxatilin. Then, a microorganism transformed with a recombinant expression vector comprising Saxatilin cDNA was prepared to manufacture recombinant Saxatilin from yeast cell in large scale. In addition, the inventors found that the recombinant Saxatilin possesses an inhibitory activity against platelet aggregation and angiogenesis which is essential for the metastasis and proliferation of tumor, without any untoward effect on normal endothelial cell proliferation, assuring that the said protein can be developed as an anti-tumor agent.

The first object of the present invention is, therefore, to provide Saxatilin derived from the venom of a Korean snake, *Agkistrodon saxatilis emelianov*.

The second object of the invention is to provide cDNA encoding Saxatilin.

The third object of the invention is to provide amino acid sequence of Saxatilin deduced from the cDNA.

The fourth object of the invention is to provide a recombinant expression vector, which produces Saxatilin in yeast cell.

The fifth object of the invention is to provide a recombinant microorganism transformed with the recombinant expression vector.

The sixth object of the invention is to provide a process for preparing recombinant Saxatilin from the transformed microorganism.

The seventh object of the invention is to provide an anti-platelet aggregation agent comprising Saxatilin.

The eighth object of the invention is to provide an anti-tumor agent comprising Saxatilin.

BRIEF DESCRIPTION OF THE DRAWINGS

The above, the other objects and features of the invention will become apparent from the following descriptions given in conjunction with the accompanying drawings, in which.

DETAILED DESCRIPTION OF THE INVENTION

Figure 1:
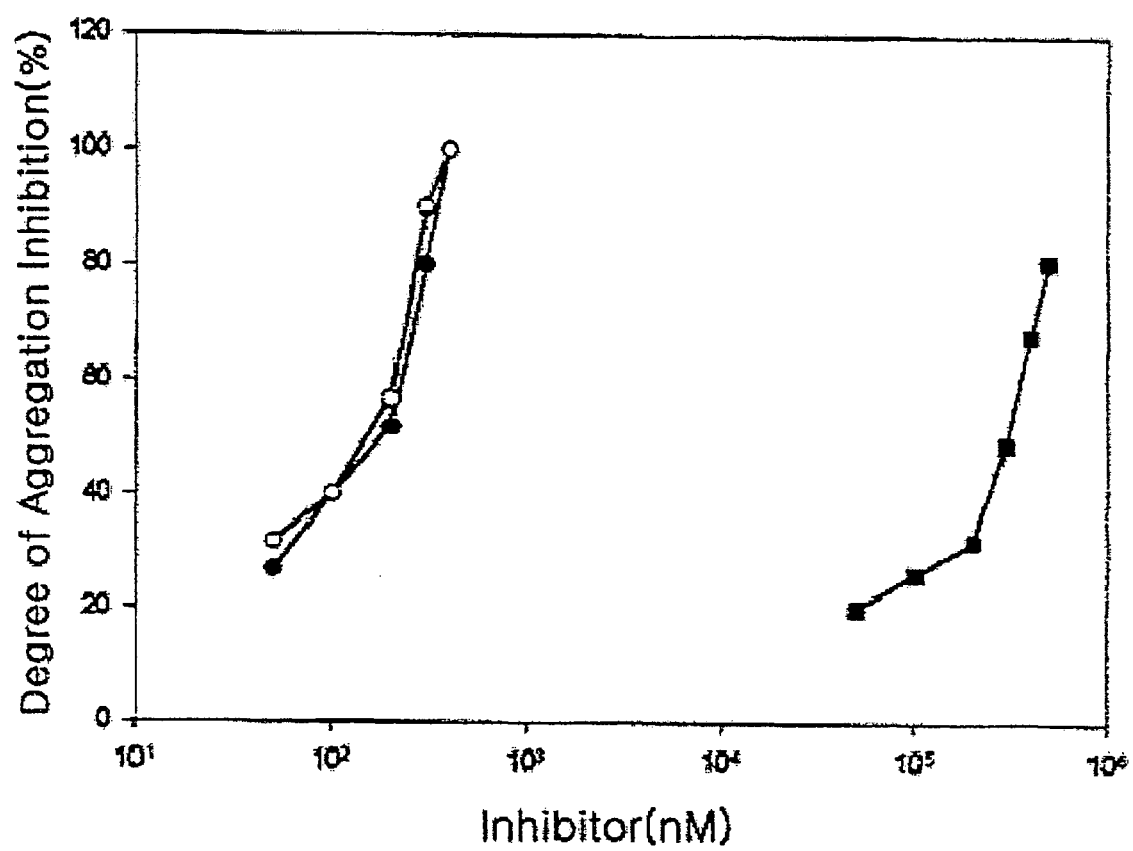
FIG. 1 is a graph showing the inhibitory activity of Saxatilin compared with those of known platelet aggregation inhibitors.

The present inventors isolated Saxatilin from the venom of a Korean snake, *Agkistrodon saxatilis emelianov* and cloned cDNA encoding Saxatilin, a recombinant expression vector comprising the cDNA, and a recombinant microorganism transformed with the recombinant expression vector, and manufactured recombinant Saxatilin by culturing the transformant.

The method of isolating Saxatilin from *Agkistrodon saxatilis emelianov* and the process for preparing recombinant Saxatilin are illustrated in more detail as follows.

The venom of *Agkistrodon saxatilis emelianov* was collected and purified by using gel-filtration column and reverse-phase HPLC, to obtain a protein possessing platelet aggregation inhibitory activity. Determination of amino acid sequence of the protein revealed that it is a novel protein and it was designated as Saxatilin. The inventors cloned cDNA encoding Saxatilin from cDNA library derived from the venom of *Agkistrodon saxatilis emelianov*. The Saxatilin cDNA was designed to contain both Xho I restriction site and protease KEX2 recognition site at N-terminal region and introduced into the EcoR I/Xho I site at C-terminal region of α-factor secretory signal protein of an expression vector, pPIC9 (8.0 kb). The expression vector encoding Saxatilin was designated as pPSAX. The expression vector may be transformed into yeast cells of *Pichia* sp., *Hansenula* sp. and *Saccharomyces* sp., preferably *Pichia* sp. such as *Pichia pastoris* GS115, SMD 1168 and KM71.

The constructed PPSAX was transformed into *Pichia pastoris* GS115 and the transformed cell was designated as "*Pichia pastoris* Y/pPSAX(*Pichia pastoris* Y/pPSAY)", and deposited with the Korean Culture Center of Microorganisms (KCCM, Hongje-1-dong 361–221, Seodaemun-gu, Seoul, Korea), an international depository authority on Jul. 21, 2000 as accession No. KCCM-10201.

The process for preparing recombinant Saxatilin comprises a step of culturing the transformed microorganism to obtain recombinant Saxatilin: The transformed cells were inoculated in the minimum glycerol media and incubated until 1.0 O.D$_{600}$ unit, harvested by centrifugation, and resuspended in the minimum methanol media and cultured in a fed-batch wise. The minimum glycerol media (pH 6.0) contained 0.5 to 1.5% of yeast extract or peptone as nitrogen source, 0.5 to 2.5% of glycerol, dextrose or glucose as carbon source and trace amounts of biotin. The minimum methanol media was the minimum glycerol media with 0.1 to 1.0% (v/v), preferably 0.3 to 0.8% (v/v), most preferably 0.5% (v/v) of methanol as carbon source. During the cell incubation in minimum glycerol media, the temperature condition was 25 to 35° C., preferably 28 to 32° C., most preferably 30° C., for 12 to 24 hr, preferably 16 to 20 hr, most preferably 18 hr. During the cell incubation in the minimum methanol media, the temperature condition was 25 to 35° C., preferably 28 to 32° C., most preferably 30° C., for 72 to 120 hr, preferably 84 to 108 hr, more preferably 96 hr.

For the purification of recombinant Saxatilin, the supernatant obtained from the cell broth by the centrifugation was applied to a hydrophobic column and HPLC, where the hydrophobic column was charged with phenyl Sepharose resin, and preferably eluted with 0.5 to 2M ammonium sulfate solution, and HPLC was equipped with source 30 RPC column and preferably eluted with 0.01 to 0.2% (v/v) TFA in acetonitrile.

The platelet aggregation-inhibitory activity of recombinant Saxatilin was compared with that of a known platelet aggregation inhibitor, recombinant Salmosin. As a result, it was demonstrated that the platelet aggregation-inhibitory activity of recombinant Saxatlilin was similar to that of recombinant Salmosin. In addition, in case of being expressed in yeast cell, the expression efficiency of Saxatilin was superior to that of Salmosin. Comparing the amino acid sequence of recombinant Saxatilin with that of Salmosin, it was confirmed that the difference in the 49$^{th}$ amino acid of two proteins brought about the different expression mode and efficiency in two proteins. Since the recombinant Salmosin contained the 48$^{th}$ and 49$^{th}$ Arg, it is readily susceptible to a signal peptidase existing in yeast, which recognizes the amino acid sequence of Lys and Arg, while the recombinant Saxatilin with 49$^{th}$ Met was rarely attacked by the same enzyme. Thus, it was understood that the 49$^{th}$ amino acid in recombinant Saxatilin plays an important role in improving expression efficiency and stability.

To investigate whether Saxatilin inhibits tumor metastasis, the effect of Saxatilin on angiogenesis was determined by HUVEC (human umbilical vein endothelial cell) assay and CAM (chick chorioallantoic membrane) assay, which were developed as the model system for the study of angiogenisis. As a result, it was demonstrated that Saxatilin inhibited angiogenesis induced by tumor. The inhibition of HUVEC proliferation by Saxatilin was due to the direct interaction of Saxatilin with Vitronectin receptor, αVβ$_3$ integrin, localized on the surface of HUVEC. It has been already known that disintegrin prevents tumor cells from binding with endothelia, leading to suppress the colony formation of the matastatic tumor. However, little has been known whether the growth of already-invaded metastatic tumor was inhibited. In this regard, the effect of Saxatilin on the metastatic tumor growth was investigated, which revealed that Saxatilin effectively inhibits the metastatic tumor growth without cytotoxicity.

The present invention is further illustrated in the following Examples, which should not be taken to limit the scope of the invention.

EXAMPLE 1

Purification of Saxatilin

To isolate Saxatilin from the venom of *Agkistrodon saxatilis emelianov*, 302.4 mg of crude venom from the snake was applied to a SEPHADEX™ G-75 gel filtration column (1.8×100 cm) equilibrated with PBS buffer, and fractionated at a flow rate of 20 ml/h. The activity of Saxatilin was determined by the platelet aggregation inhibition assay: The concentrated human platelet rich plasma (PRP) obtained from 400 ml of human blood was diluted to the concentration of 300,000 platelets/μl. The diluted PRP (450 μl) was mixed with 50 μl of PBS and then incubated in the aggregometer CHROMO-LOGT™, USA) at 37° C. for 3 minutes. After collagen (2 nM) was added into the PRP solution to induce the platelet aggregation, the difference of light transmittance was measured.

The active fractions showing the inhibitory effect on the platelet aggregation contained a protein whose molecular weight ranges from 7 kD to 10 kD in Native-PAGE gel. The pooled active fractions were applied to a reverse-phase HPLC (C18) column (7.8×300 mm) equilibrated with distilled water containing 0.1% (v/v) TFA, eluted by the linear gradient of 5–45% acetonitrile with 0.1% (v/v) TFA. Saxatilin was eluted at the point of 21% acetonitrile with the purification yield of 0.2%.

EXAMPLE 2

Amino Acid Sequence Analysis of Saxatilin

To analyze the amino acid sequence of Saxatilin, the purified Saxatilin was electrophoresed on SDS-PAGE gel under the reducing condition and electroblotted onto polyvinylidene difluoride (PVDF) membrane (Biorad, USA). The N-terminal amino acid sequence of Saxitilin was determined to be GEECDCGAPANP (SEQ ID NO:9) by automated protein sequence analyzer.

EXAMPLE 3

Determination of the Molecular Weight of Saxatilin by Mass Spectrometer

The molecular weight of Saxatilin was determined as three different forms of 7,444, 7,515 and 7,647 Da by the aid of Mass spectrometer KRATOS KOMPACT MOLD II™, KRATOS ANALYTICAL™, Manchester, U.K.), which is ascribed to three types of isoforms containing N-terminal sequences of 'EAGEE' and 'AGEE', in addition to 'GEE'.

EXAMPLE 4

Determination of DNA Sequence Encoding Saxatilin

For the cloning of Saxatilin cDNA, mRNA was extracted from the venom gland of *Agkistrodon saxatilis emelianov* using oligo-dT cellulose. cDNA library was constructed by using a template of mRNA obtained from the venom gland, and oligo-dT primer and reverse transcriptase. Then, 5' primer was designed by deduction from the N-terminal sequence, which is 5'-GGNGARGARTGYGAYTGYGG-3' (SEQ ID NO:3): primer 1. The 3' primer was designed by deduction from the C-terminal sequence, determined during subcloning process, which is 5'-GGCATGGAAGG-GATTTCTGG-3' (SEQ ID NO:4): primer 2. The polymerase chain reaction (PCR) was performed using the 5' primer, the 3' primer and a template of the synthesized cDNA library of venom gland. The PCR products of 220 bp separated on agarose gel electrophoresis were subcloned into pGEM-T vector (PROMEGA™, USA) and used to analyze the DNA sequence encoding Saxatilin (SEQ ID NO:2). The total amino acid sequence of Saxatilin was deduced from the cloned cDNA sequence (SEQ ID NO:1).

EXAMPLE 5

Comparison of the Inhibitory Effect of Saxatilin with Known Peptides Possessing Platelet Aggregation Inhibitory Activity For the comparison of the inhibitory effect of Saxatilin with those of other known peptides possessing platelet aggregation inhibitory activity, Salmosin (see: Korean Patent No. 142606, SEQ ID NO:10) and GRGDSP (SEQ ID NO:7), the platelet aggregation inhibition assay was performed as follows: 225 µl of the human platelet rich plasma (300,000 platelets/L) was mixed with 25 µl of the platelet aggregation inhibitor peptide solutions in PBS and then incubated in aggregometer (CHROMO-LOGT™, USA) at 25° C. for 5 minutes. After ADP was added into each of the PRP solutions to induce the platelet aggregation, the turbidity was measured, respectively (see: FIG. 1). In FIG. 1, (•) represents the degree of platelet aggregation inhibition of Saxatilin; (○), Salmosin (SEQ ID NO: 10); and (■), GRGDSP (SEQ ID NO: 7), respectively. As shown in FIG. 1, $IC_{50}$ value of Saxatilin was 179 nM, which is comparable with 173 nM of Salmosin, and has a 1000 times more potent inhibitory effect than GRGDSP (SEQ ID NO:7) peptide.

EXAMPLE 6

Cloning of Saxatilin DNA

The PCR (ROBOCYCLERTM, STRATAGENE™, USA) was performed using a plasmid containing Saxatilin cDNA, prepared from Example 4, as a template and the following two primers:

N-terminal primer, containing both Xho I restriction site and protease KEX2 recognition site, 5'-CCGCTC-GAGAAAAGAGAGGCCGGAGAAGAATGT-3' (SEQ ID NO:5).

C-terminal primer, containing both EcoR I restriction site and two stop codons, 5'-CGGAATTCTCATTAGGCATG-GAAGGGA-3' (SEQ ID NO:6).

Figure 2:
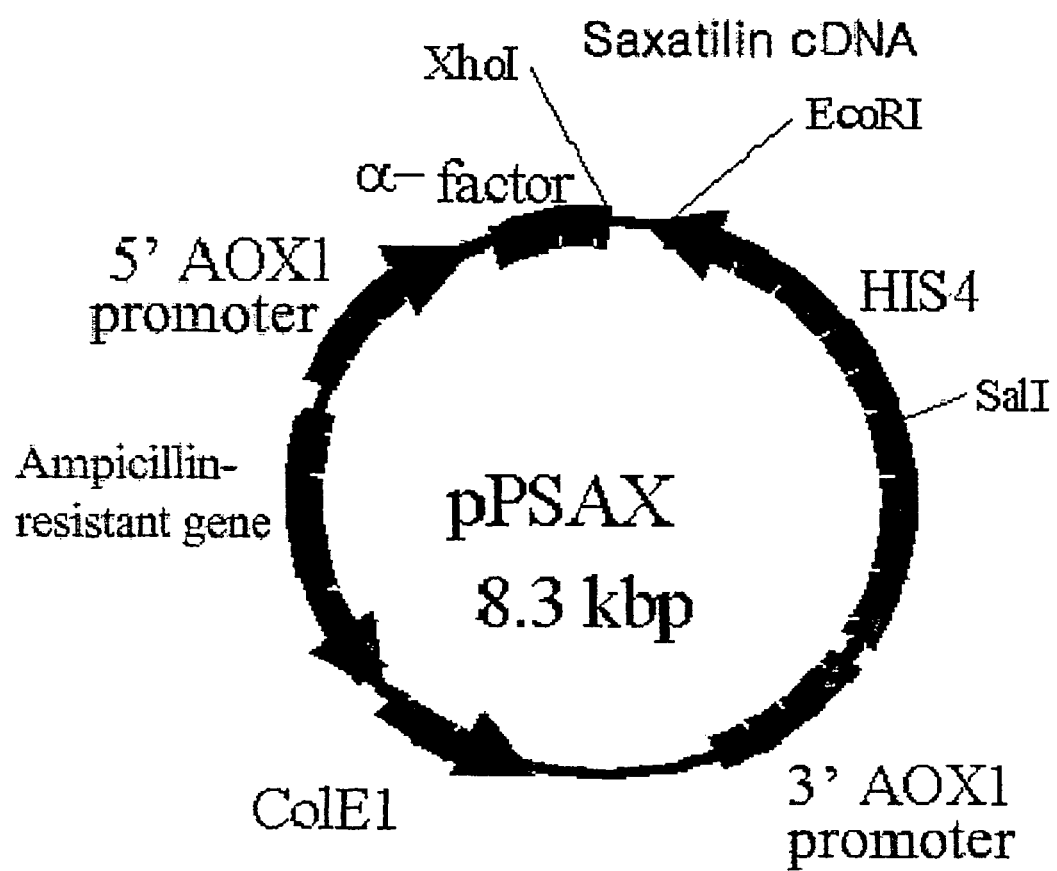
FIG. 2 is a gene map of recombinant Saxatilin expression vector, pPSAX.

The PCR was carried out for 30 cycles of 1 mm at 94° C. (denaturation), 1 mm at 55° C. (annealing), and 1 mm at 72° C. (polymerization), respectively. The DNA fragments of about 250 bp, PCR products, were cloned into pBlue-scriptKS (2.9 kb, STRATAGENE™, USA) by the reaction with T4 DNA ligase to construct a recombinant plasmid. The recombinant plasmid was used for the transformation of *E.coli* XL-1Blue. The transformed *E.coli* was incubated on LB (Luria Botani) plate with 100 pg/ml of ampicillin and selected by formed white colony. The plasmid extracted from the white colony was investigated using restriction map analysis and DNA sequence analysis (ALF SYSTEM™, AMERSHAM PHARMACIA BIOTECH™, USA), and thus confirmed that the DNA fragment of 250 bp by PCR was Saxatilin cDNA. The EcoR I/Xho I fragment of the plasmid was cloned into the C-terminal region of the α-factor secretory signal protein of an expression vector pPIC9 (8.0 kb), to give an expression vector comprising Saxatilin encoding cDNA, pPSAX (8.3 kbp) (see: FIG. 2).

The pPSAX was digested with SaII to give a linear DNA fragment and dissolved in TB buffer at a concentration of 0.5 µl/µl, which was then mixed with 80 µl of *Pichia pastoris* GS 115 competent cell (INVITROGEN™, USA) to perform transformation by electroporator (BIORAD GENE PULSER™, USA) under a condition of 1.5 kV. The transformed cells were spread onto a histidine-deficient agar plate and incubated at 30° C. for 3 days. The selected colonies were inoculated to 1L of minimum glycerol media (100 mM sodium phosphate pH 6.0, yeast nitrogen base 1.34%, biotin $4\times10^{-5}$%, glycerol 1%) and incubated at 30° C. until $O.D_{600}$ unit reaches to the level of 1.0. At-the end of the incubation period, the cells were harvested by centrifligation at 3000 xg, and resuspended in the minimum methanol media (containing 100 mM sodium phosphate pH 6.0, yeast nitrogen base 1.34%, biotin $4\times10^{-5}$%, methanol 0.5%). These cells were grown at 30° C. and induced the expression of recombinant Saxatilin. The cells were further incubated for 96 hr with the addition of 0.5% methanol at an interval of 24 hour, and it was confirmed that Saxatilin was accumulated in the media during the incubation period. The transformed cell containing Saxatilin expression vector, pPSAX, was designated as "*Pichia pastoris* Y/pPSAX (*Pichia pastoris* Y/pP-SAX)", and deposited with the Korean Culture Center of Microorganisms (KCCM, Hongje-1-dong 361–221, Seodae-mun-gu, Seoul, Korea), an international depository authority as accession No. KCCM-10201 on Jul. 21, 2000.

For the purification of Saxatilin, the supernatant obtained from cell broth by the centrifugation at 5,000 xg was applied to a phenyl Sepharose column of 1.3×20 cm (BIO RAD™, USA) equilibrated with 1.5 M ammonium sulfate solution, and eluted with 1 M ammonium sulfate solution at a flow rate of 20 ml/hour to obtain active fractions of Saxatilin. The activity of Saxatilin was determined in a similar manner as in Example 1. The active fractions were loaded into HPLC column (source 30 RPC column, 7.8×300 mm) equilibrated in distillated water with 0.1% (v/v) TFA, and eluted by the linear gradient of 0 to 50% (v/v) acetonitrile to give pure Saxatilin with a purification yield of 107 mg/L.

EXAMPLE 7

Inhibition of Platelet Aggregation by Recombinant Saxatilin

Recombinant Saxatilin obtained in Example 6 was assayed by the platelet aggregation inhibition method described in Example 1, and compared with those of wild-type Saxatilin obtained in Example 1 and GRGDSP (SEQ ID NO:7) (see: Table 1), respectively.

As shown in Table 1 below, the recombinant Saxatilin represented the comparable platelet aggregation inhibitory activity with the wild-type Saxatilin.

TABLE 1

| $IC_{50}$ determined by platelet aggregation inhibition assay | |
|---|---|
| Inhibitor | $IC_{50}$ (nM) |
| Wild-type Saxatilin | 136 |
| Recombinant Saxatilin | 139 |
| GRGDSP (SEQ ID NO: 7) | $270 \times 10^3$ |

EXAMPLE 8

Anti-Platelet Aggregation Activity of Saxatilin

When a mixture of collagen and epinephrine was injected into mice intravenously, thrombus was formed in pulmonary artery, which led to paralysis, dilation of pupil, laboring breath and convulsions, and finally 70% of the mice died not more than 5 min. Thus, it was investigated whether the intravenous injection of recombinant Saxatilin could reduce the thrombosis symptoms.

At 10 minutes after Saxatilin (0, 0.1, 0.25 and 0.5 mg/kg dissolved in 0.1 ml PBS, respectively) was intravenously injected into the tails of ICR mice, the mixture of collagen and epinephrine (120 μg collagen and 12 μg epinephrine in 0.1 ml PBS) was also injected into the tails of ICR mice, intravenously, and the viability was determined (see: Table 2).

TABLE 2

|  | Saxatilin (mg/kg) | | | |
|---|---|---|---|---|
| Treatment | 0 | 0.1 | 0.25 | 0.5 |
| Mortal group/ Total group | 18/20 | 16/20 | 11/20 | 3/20 |
| Viability | 10 | 20 | 55 | 85 |

As shown in Table 2, based on the results that the treatment of Saxatilin caused the increase in viability, Saxatilin was supposed to suppress the coagulation induced by collagen and epinephrine, with more potent inhibitory activity in case of pre-treatment than post-treatment.

EXAMPLE 9

Effect of Recombinant Saxatilin on Human Umbilical Vein Endothelial Cell (HUVEC)

It has been known that disintegrins containing RGD sequence which is a part of recombinant Saxatilin (49–51 amino acid sequence), suppress the bFGF-stimulated endothelial cell growth. To investigate whether recombinant Saxatilin containing RGD sequence inhibits the endothelial cell proliferation, proliferation inhibition assay was performed using HUVEC. The activity of Saxatilin was compared with that of Salmosin (SEQ ID NO:10), which is known to inhibit the bFGF-stimulated endothelial cell proliferation.

Figure 3:
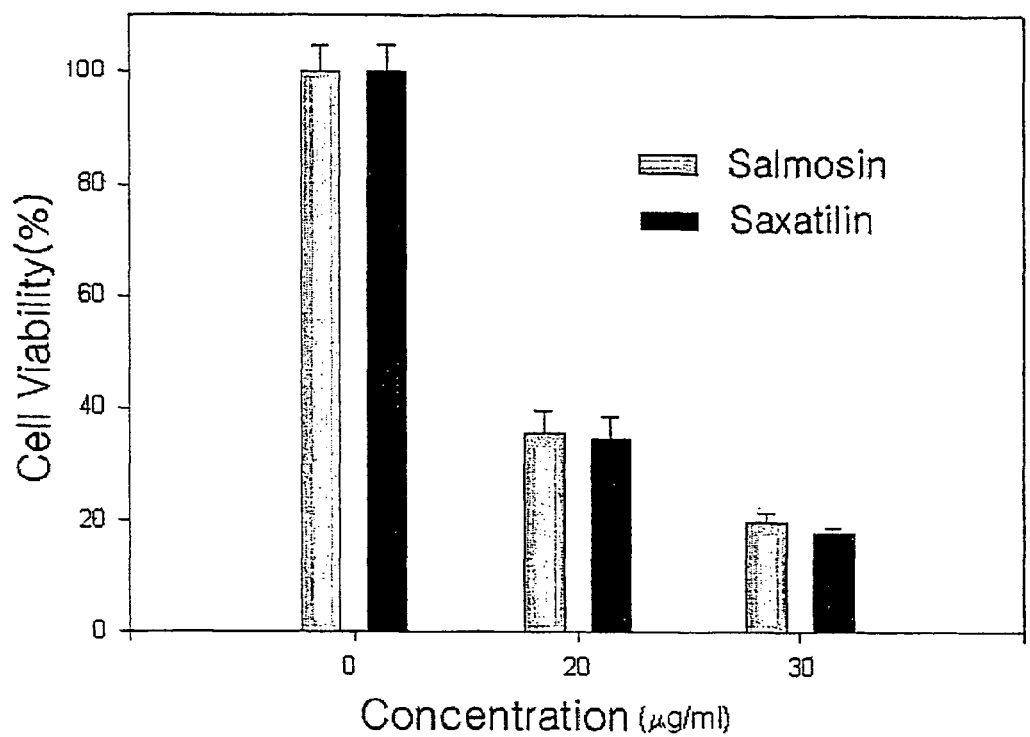
FIG. 3 is a graph showing the effect of recombinant Saxatilin on HUVEC growth compared with that of Salmosin.

HUVEC was cultured on 24-well microplate coated with gelatin at 37° C. for 24 hr under an environment of 5% $CO_2$. After the media was replaced with 0.25 ml DMEM containing 5% fetal bovine serum, recombinant Saxatilin obtained from Example 6 and Salmosin were added in a concentration of 0, 20, and 30 μg/ml, respectively. Then, cells were further incubated for 20 min and treated with 1 ng/ml of bFGF solution. After incubation of 72 hr, cells were trypsinized and the cell numbers were counted to determine cell viability (see: FIG. 3). As shown in FIG. 3, Saxatilin inhibited the HUVEC growth in a dose-dependent manner similarly as Salmosin.

EXAMPLE 10

Inhibition of HUVEC Adhesion by Saxatilin

To confirm that inhibition of HUVEC proliferation by Saxatilin is due to the direct interaction of Saxatilin with Vitronectin receptor, $\alpha V \beta_3$ integrin, localized on the HUVEC surface, it was investigated whether Saxatilin blocks HUVEC from binding to Vitronectin-coated 96-well plate.

Figure 4A:
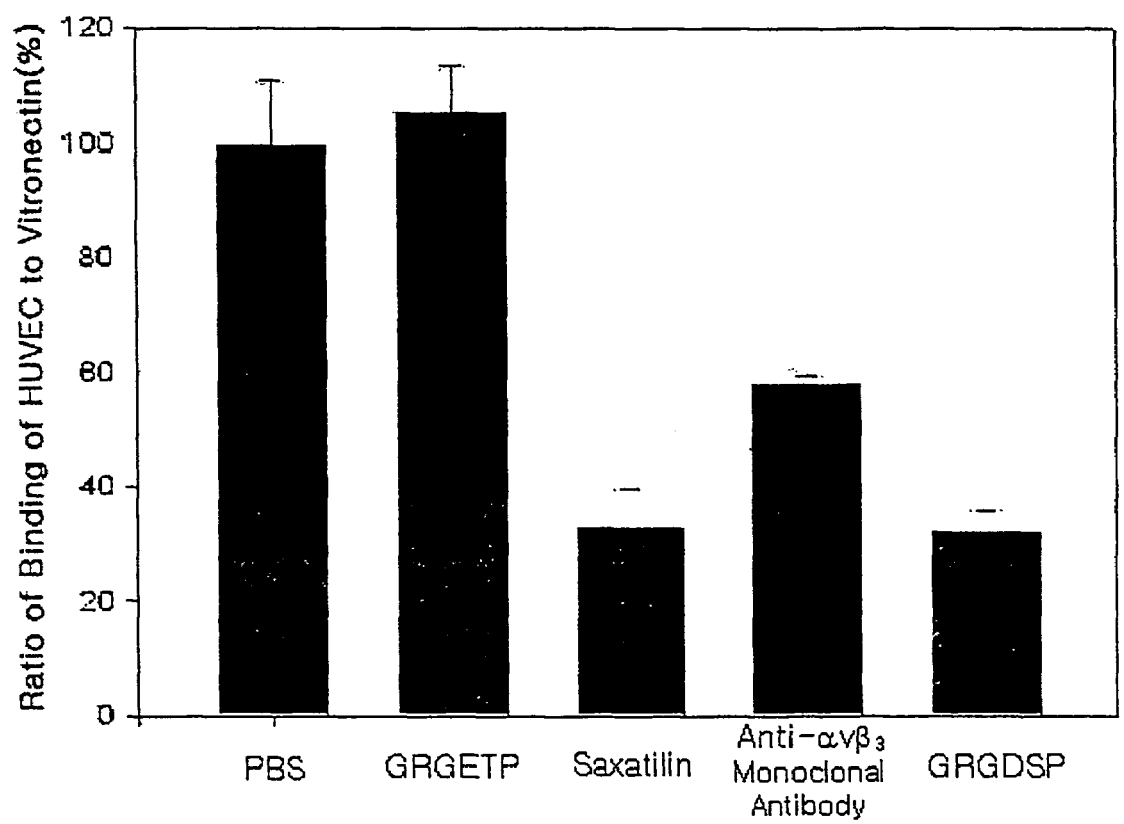
FIG. 4a is a graph showing the effect of anti-αVβ3 monoclonal antibody, GRGDSP (SEQ ID NO:7), GRGETP (SEQ ID NO:8) and recombinant Saxatilin on the binding of Vitronectin to HUVEC.
Figure 4B:
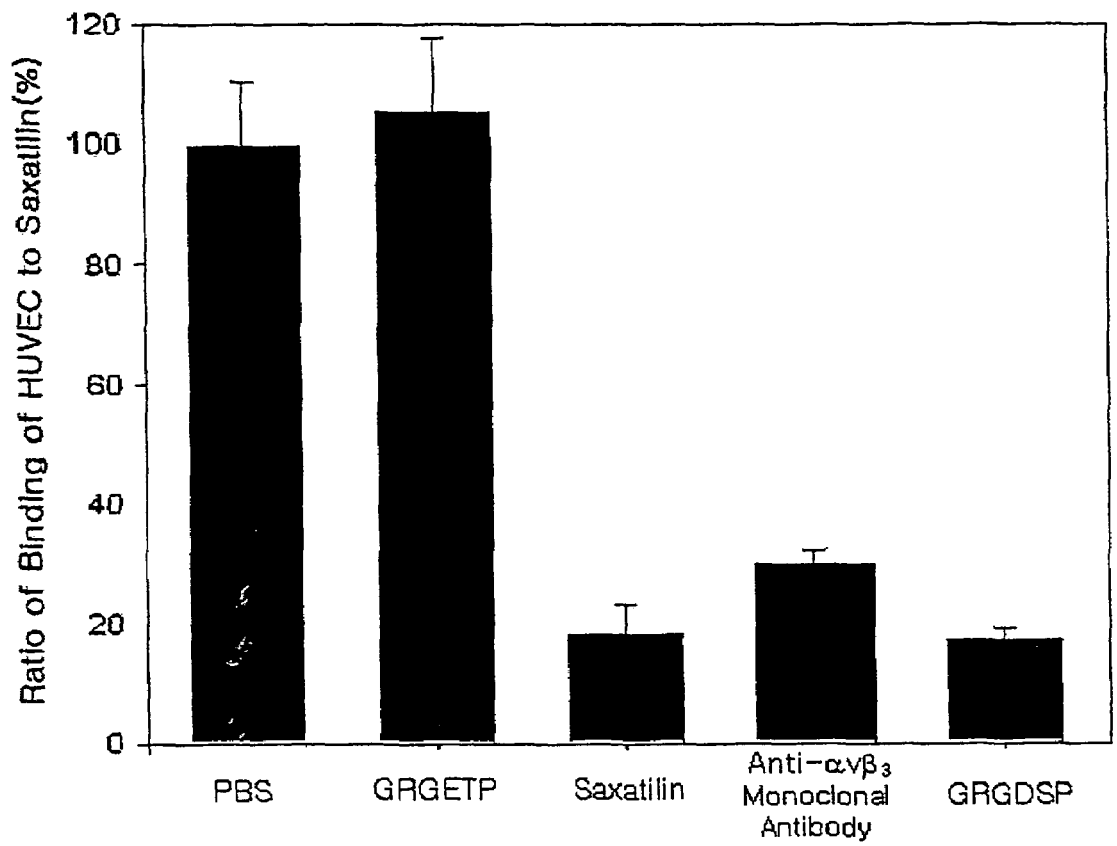
FIG. 4b is a graph showing the effect of anti-αVβ3 monoclonal antibody, GRGDSP (SEQ ID NO:7), GRGETP (SEQ ID NO:8) and recombinant Saxatilin on the binding of Saxatilin to HUVEC.

96-well plate was coated with recombinant Saxatilin obtained in Example 6 (1 μg/well) as well as Vitronectin (0.5 μg/well) which were dissolved in phosphate buffered saline (PBS) for 16 hr at 4° C. After washing the plate, 10 mg/ml of heat-treated bovine serum albumin (BSA) was added for blocking of uncharged protein binding site. The plate was incubated for 1 hr and washed with PBS. HUVEC was trypsinized and washed with PBS three times, and then, resuspended in serum-free DMEM. $5 \times 10^4$ cells were mixed with anti-$\alpha V \beta_3$ monoclonal antibody, a synthesized RGD peptide, GRGDSP (SEQ ID NO:7), a synthesized RGE peptide, GRGETP (SEQ ID NO:8) and Saxatilin, and pre-incubated for 20 min at 37° C. Then, the mixture was added to the wells of both Saxatilin and Vitronectin-coated 96-well plate. After 1 hr of incubation at 37° C. under an environment of 5% $CO_2$, the plate was washed with PBS to remove unbound cells, and bound cells were fixed and stained with Coomassie blue. Optical absorbences of the wells were measured at 540 nm to count relative cell numbers (see: FIGS. 4a and 4b).

As shown in FIGS. 4a and 4b, pre-incubation of bFGF-stimulated HUVEC with GRGDSP (SEQ ID NO:7), Saxatilin and anti-$\alpha V \beta_3$ monoclonal antibody prevented HUVEC from adhering to Vitronectin (see: FIG. 4a) and Saxatilin inhibited (see: FIG. 4b) as well, indicating that Saxatilin inhibited integrin-mediated cell adhesion by binding with $\alpha V \beta_3$ integrin on HUVEC surface.

EXAMPLE 11

Figure 5A:
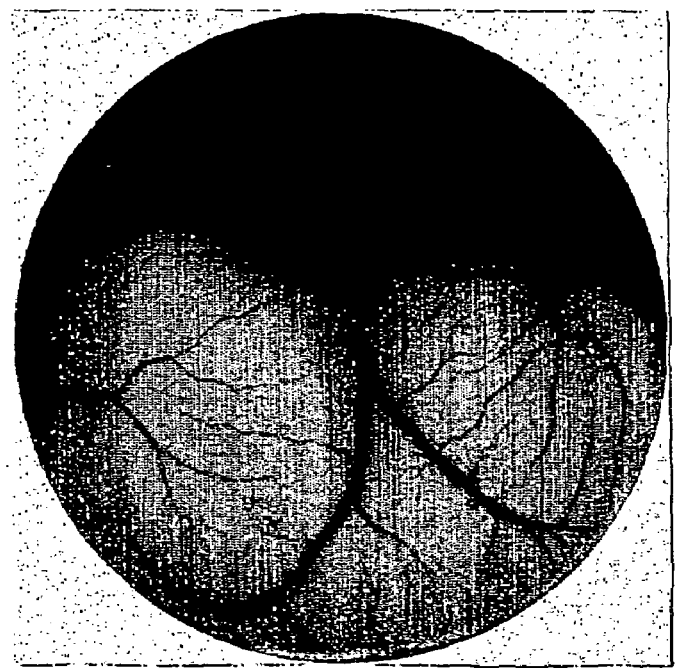
FIG. 5a is a photograph showing the bFGF-stimulated angiogenesis of the CAM (chick chorioallantoic membrane).
Figure 5B:
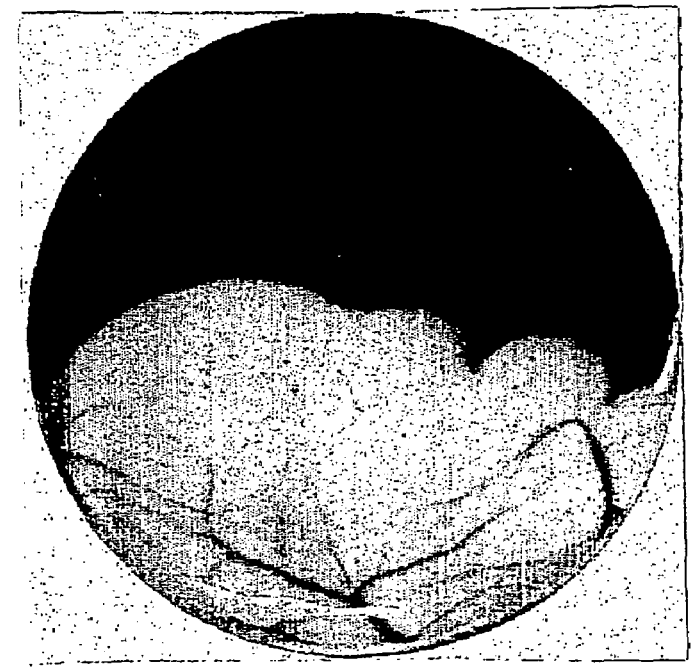
FIG. 5b is a photograph showing the effect of recombinant Saxatilin on CAM angiogenesis.

Effect of Saxatilin on Angiogenesis by Chick Chorioallantoic Membrane (CAM) Assay Chick chorioallantoic membrane (CAM) assay, a simulated in vivo model, was carried out to examine the effect of Saxatilin on bFGF-stimulated angiogenesis. A part of the rind of fertilized 3-day-old egg was broken carefully, and sealed with transparent tape, and incubated for 10 days at 37° C. under an environment of 60% humidity. Then, bFGF was applied to the chick chorioallantoic membrane (CAM) of individual embryo (6 ng/embryo) to induce angiogenesis. After further incubation of 24 hr, PBS as a negative control and 5 μg recombinant Saxatilin obtained from Example 6 were applied to CAM, respectively. At 72 hr after treatment, the blood vessels of embryos were observed (see: FIGS. 5a and 5b). As shown in FIGS. 5a and 5b, PBS showed no effect (see: FIG. 5a) while Saxatilin had an inhibitory effect on angiogenesis (see: FIG. 5b).

EXAMPLE 12

Inhibitory Effect of Saxatilin on Metastatic Tumor Growth

Disintegrins suppress the lung tumor colony formation by preventing tumor cells from adhering to endothelial cells. However, it has never been reported that disintegrins inhibit the metastatic tumor promotion. Therefore, it was investigated whether Saxatilin has an effect on the metastatic tumor growth.

$1 \times 10^6$ Lewis lung carcinoma cells (purchased from American Type Cell Culture, Rockville, Md., USA) were injected into the tails of 8-week-old male C57BL/6 mice (Charles river, Japan), intravenously. At 4 day after injection, recombinant Saxatilin obtained from Example 6 was periodically applied to mice by intravenous injection in an amount of 1.25 mg/kg/day (once per day). After 4-weeks of periodical treatment, tumor-bearing mice were sacrificed, and the number of tumor colony was counted by using stereomicroscope. As a result, it was clearly demonstrated that Saxatilin potently inhibited the metastatic tumor growth (see: Table 3).

TABLE 3

Suppression of metastatic Lewis lung carcinoma growth by Saxatilin

| Saxatilin (mg/kg mouse) | Number of tested mice | Average colony number | Inhibition rate (%) |
|---|---|---|---|
| 0 | 4 | 15 ± 6 | 0 |
| 1.25 | 4 | 0.7 ± 0.6 | 95 |

The suppression of metastatic tumor growth by Saxatilin was ascribed to the anti-angiogenesis effect of Saxatilin, which potently inhibited the bFGF-stimulated BCE cell proliferation by blocking of αVβ3 integrin function essential for angiogenesis. In addition, Saxatilin showed no toxicity on tested mice.

Figure 6A:
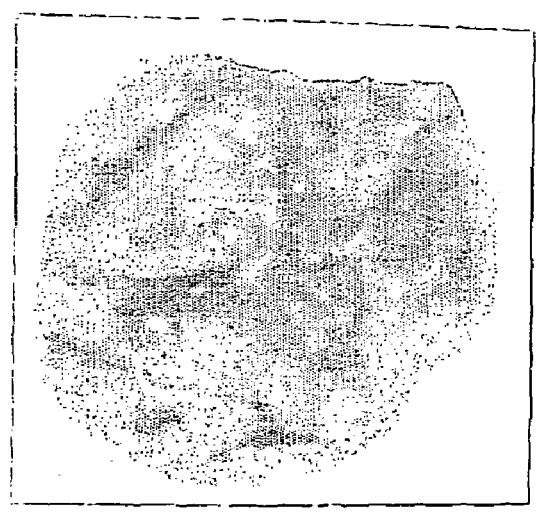
FIG. 6a is a photograph showing the normal lung tissue without Lewis lung cancer cells.
Figure 6B:
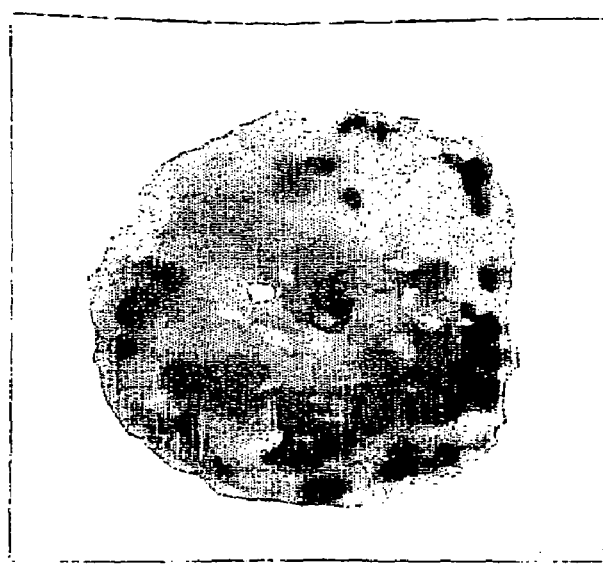
FIG. 6b is a photograph showing the lung tissue injected with Lewis lung cancer cells and treated with PBS control.
Figure 6C:
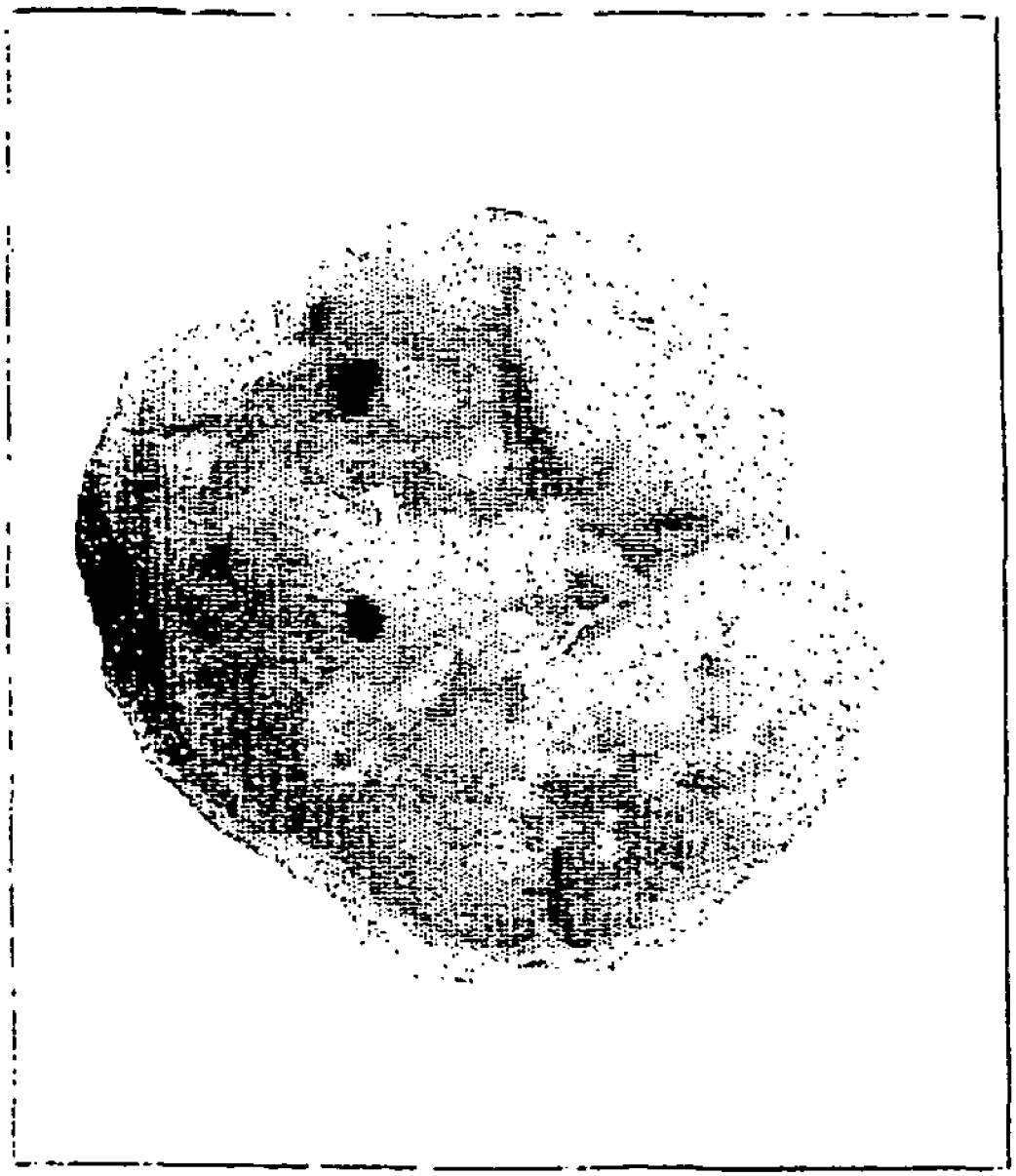
FIG. 6c is a photograph showing the lung tissue injected with Lewis lung cancer cells and treated with recombinant Saxatilin.

Furthermore, to observe the direct effect of Saxatilin on the metastatic lung carcinoma, histochemical study was carried out. Tumor-bearing lung tissue was fixed in paraffin in accordance with the conventionally known method followed by treatment of Bouin's solution for 4 hours. The tissue section of 4 μm thickness was infiltrated with trypsin at 37° C. for 10 min and washed with PBS. The tissue section was stained with hematoxylin and eosin, and then mounted (see: FIGS. 6a, 6b and 6c). FIG. 6a is a photograph showing lung tissue without Lewis lung carcinoma cell; FIG. 6b, lung tissue implanted with Lewis lung carcinoma cell and then treated with PBS; and, FIG. 6c, lung tissue implanted with Lewis lung carcinoma cell and then treated with Saxatilin. As shown in FIGS. 6b and 6c, the metastatic tumor growth was observed in control group treated with PBS evidently (see: FIG. 6b), while not observed in Saxatilin-administered group (see: FIG. 6c). As illustrated as above, it was assumed that the suppression of metastatic tumor growth in Saxatilin-treated mice was due to blockade of Saxatilin against angiogenesis, which was essential for the secondary tumor growth.

Administration and Effective Dose

The pharmaceutical composition of the present invention, which comprises an active ingredient of Saxatilin and pharmaceutically acceptable carrier may be administered as an injectable form. The injectable form may further comprise sterilized isotonic aqueous solution or suspension, and the pharmaceutically acceptable carrier covers preservatives, stabilizers, wetting agents, emulsifiers, salts for changing osmotic pressure or buffers. Though the effective dose of Saxatilin is variable depending on age, body weight of the patient and progression of the disease, it is preferable to administer parenterally 20 to 52 mg/60 kg/day in a single dose for the treatment of thrombosis, and 30 to 120 mg/60 kg/day in a single dose for the treatment of cancer, which may be individualized by experience of the skilled in the art.

Acute Toxicity

To examine the acute toxicity of Saxatilin as anti-platelet aggregation agent and anti-tumor agent, Saxatilin was injected into male C57BL/6 mouse subcutaneously and the dead were counted to determine $LD_{50}$ for 7 days. As a result, $LD_{50}$ was determined as about 1100 mg/kg, indicating that the anti-platelet aggregation agent and anti-tumor agent comprising Saxatilin were sufficiently safe within the range of the effective dose.

As clearly illustrated and demonstrated as above, the present invention provides Saxatilin, a protein derived from the venom of a Korean snake, *Agkisrodon saxatilis emelianov*, a process for preparing the same, anti-platelet aggregation agent and anti-tumor agent comprising an active ingredient of Saxatilin. The present inventors purified Saxatilin from the venom of *Agkistrodon saxatilis emelianov*, cloned cDNA encoding Saxatilin, and constructed a recombinant expression vector comprising the cDNA and a recombinant microorganism transformed with the recombinant expression vector which expresses Saxatilin, and prepared Saxatilin by culturing the recombinant microorganism.

Saxatilin effectively suppresses the platelet aggregation and angiogenesis of tumor cells, which makes possible its practical application as an active ingredient of anti-platelet agent and anti-tumor agent.

Although the preferred embodiments of the present invention have been disclosed for illustrative purpose, those who are skilled in the art will appreciate that various modifications, additions and substitutions are possible, without departing from the scope and spirit of the invention as described in the accompanying claims.

What is claimed is:

1. An isolated and purified nucleic acid molecule comprising the nucleotide sequence of SEQ ID NO:2.

2. An isolated and purified polypeptide comprising the amino acid sequence of SEQ ID NO:1.

3. A process for preparing a polypeptide comprising the amino acid sequence of SEQ ID NO:1 comprising the steps of:
   (i) gel filtration of venom collected from *Agkistrodon saxatilis emelianov* to obtain an active fraction having an inhibitory effect on platelet aggregation; and,
   (ii) applying the active fraction to high performance liquid chromatography to purify a polypeptide comprising the amino acid sequence of SEQ ID NO:1.

4. An expression vector comprising the nucleic acid molecule of claim 1.

5. A biologically pure culture of *Pichia pastoris* Y/pPSAX (KCCM-10201) which is obtained by transforming the expression vector of claim 4 into *Pichia pastoris* GS115.

6. A process for preparing a recombinant polypeptide comprising the amino acid sequence of SEQ ID NO:1 which comprises a step of culturing a microorganism transformed with an expression vector containing the nucleic acid molecule of claim 1 to obtain a recombinant polypeptide comprising the amino acid sequence of SEQ ID NO:1.

7. The process for preparing the recombinant polypeptide of claim 6, wherein the expression vector is pPSAX.

8. The process for preparing the recombinant polypeptide of claim 6, wherein the transformed microorganism is *Pichia pastoris* Y/pPSAX (KCCM-10201).

9. The process for preparing the recombinant polypeptide of claim 8, wherein the transformed microorganism is cultured under conditions of pH 5.5 to 6.5, 25° C. to 35° C. for 12 to 24 hours, harvested by centrifugation and cultured again in a medium containing 0.5% to 1.5% (v/v) methanol under conditions of pH 5.5 to 6.5, 25° C. to 35° C. for 72 to 120 hours.

10. The process for preparing the recombinant polypeptide of claim 8, wherein supernatant from a culture containing the transformed microorganism is collected and subjected to a hydrophobic column and high performance liquid chromatography.

11. A pharmaceutical composition comprising a polypeptide comprising the amino acid sequence of SEQ ID NO:1 and a pharmaceutically acceptable carrier.

12. The pharmaceutical composition of claim 11, wherein said composition is an anti-tumor agent.

13. The pharmaceutical composition of claim 11, wherein said composition is an anti-platelet aggregation agent.

* * * * *

SEQUENCE LISTING

<160> NUMBER OF SEQ ID NOS: 10

<210> SEQ ID NO 1
<211> LENGTH: 73
<212> TYPE: PRT
<213> ORGANISM: Agkistrodon saxatilis emelianov

<400> SEQUENCE: 1

Glu Ala Gly Glu Glu Cys Asp Cys Gly Ala Pro Ala Asn Pro Cys Cys
1               5                   10                  15

Asp Ala Ala Thr Cys Lys Leu Arg Pro Gly Ala Gln Cys Ala Glu Gly
            20                  25                  30

Leu Cys Cys Asp Gln Cys Arg Phe Met Lys Gly Thr Ile Cys Arg
        35                  40                  45

Met Ala Arg Gly Asp Asp Met Asp Asp Tyr Cys Asn Gly Ile Ser Ala
    50                  55                  60

Gly Cys Pro Arg Asn Pro Phe His Ala
65                  70

<210> SEQ ID NO 2
<211> LENGTH: 213
<212> TYPE: DNA
<213> ORGANISM: Agkistrodon saxatilis emelianov

<400> SEQUENCE: 2
ggagaagaat gtgactgtgg cgctcctgca aatccgtgct gcgatgctgc aacctgtaaa      60
ctgagaccag gggcgcagtg tgcagaagga ctgtgttgtg accagtgcag atttatgaaa    120
gaaggaacaa tatgccggat ggcaagggt gatgacatgg atgattactg caatggcata    180
tctgctggct gtcccagaaa tcccttccat gcc                                 213

<210> SEQ ID NO 3
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(20)
<223> OTHER INFORMATION: where n may be a or g or c or t/u, other, or
      unknown

<400> SEQUENCE: 3
ggngargart gygaytgygg                                                 20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ggcatggaag ggatttctgg                                                 20

<210> SEQ ID NO 5
<211> LENGTH: 33
<212> TYPE: DNA
<213> ORGANISM: Artificial Sequence
<220> FEATURE:
<223> OTHER INFORMATION: primer -continued

```
<400> SEQUENCE: 5
ccgctcgaga aaagagaggc cggagaagaa tgt                                    33

<210> SEQ ID NO 6
<211> LENGTH: 27
<212> TYPE: DNA
<213> ORGANISM: Artificial Sequence
<220> FEATURE:
<223> OTHER INFORMATION: primer

<400> SEQUENCE: 6
cggaattctc attaggcatg gaaggga                                           27

<210> SEQ ID NO 7
<211> LENGTH: 6
<212> TYPE: PRT
<213> ORGANISM: Artificial Sequence
<220> FEATURE:
<223> OTHER INFORMATION: oligopeptide

<400> SEQUENCE: 7

Gly Arg Gly Asp Ser Pro
1               5

<210> SEQ ID NO 8
<211> LENGTH: 6
<212> TYPE: PRT
<213> ORGANISM: Artificial Sequence
<220> FEATURE:
<223> OTHER INFORMATION: oligopeptide

<400> SEQUENCE: 8

Gly Arg Gly Glu Thr Pro
1               5

<210> SEQ ID NO 9
<211> LENGTH: 12
<212> TYPE: PRT
<213> ORGANISM: Agkistrodon saxatilis emelianov

<400> SEQUENCE: 9

Gly Glu Glu Cys Asp Cys Gly Ala Pro Ala Asn Pro
1               5                   10

<210> SEQ ID NO 10
<211> LENGTH: 73
<212> TYPE: PRT
<213> ORGANISM: Agkistrodon halys brevicaudus

<400> SEQUENCE: 10

Glu Ala Gly Glu Glu Cys Asp Cys Gly Ser Pro Gly Asn Pro Cys Cys
1               5                   10                  15

Asp Ala Ala Thr Cys Lys Leu Arg Gln Gly Ala Gln Cys Ala Glu Gly
            20                  25                  30

Leu Cys Cys Asp Gln Cys Arg Phe Met Lys Glu Gly Thr Ile Cys Arg
        35                  40                  45

Arg Ala Arg Gly Asp Asp Leu Asp Asp Tyr Cys Asn Gly Ile Ser Ala
    50                  55                  60

Gly Cys Pro Arg Asn Pro Phe His Ala
65                  70
```